(12) United States Patent
Zabudkin et al.

(10) Patent No.: US 9,035,032 B2
(45) Date of Patent: May 19, 2015

(54) METHOD FOR PREPARING 4-DEMETHYLDAUNORUBICIN

(75) Inventors: Alexander F. Zabudkin, Donetsk (UA); Victor Matvienko, Donetsk (UA); Alexey Matveev, Donetsk (UA); Aleksandr M. Itkin, San Diego, CA (US)

(73) Assignee: SOLUX CORPORATION, San Diego, CA (US)

( * ) Notice: Subject to any disclaimer, the term of this patent is extended or adjusted under 35 U.S.C. 154(b) by 1422 days.

(21) Appl. No.: 11/610,033

(22) Filed: Dec. 13, 2006

(65) Prior Publication Data

US 2007/0135624 A1    Jun. 14, 2007

Related U.S. Application Data

(60) Provisional application No. 60/749,464, filed on Dec. 13, 2005.

(51) Int. Cl.
*C07H 15/24*    (2006.01)

(52) U.S. Cl.
CPC ..................................... *C07H 15/24* (2013.01)

(58) Field of Classification Search
None
See application file for complete search history.

(56) References Cited

U.S. PATENT DOCUMENTS

| | | | |
|---|---|---|---|
| 3,803,124 A | 4/1974 | Arcamone | |
| 4,112,076 A | 9/1978 | Arcamone | |
| 4,188,377 A | 2/1980 | Suarato et al. | |
| 4,211,864 A | 7/1980 | Vicario et al. | |
| 4,345,068 A | 8/1982 | Suarato et al. | |
| 4,471,052 A * | 9/1984 | Mitscher et al. | 435/78 |
| 4,499,083 A * | 2/1985 | Umezawa et al. | 514/36 |
| 4,861,870 A | 8/1989 | Oppico | |
| 5,091,373 A | 2/1992 | Gatti et al. | |
| 5,731,313 A | 3/1998 | Suarato et al. | |
| 5,814,608 A | 9/1998 | Animati et al. | |
| 5,874,550 A | 2/1999 | van der Rijst et al. | |
| 5,945,518 A | 8/1999 | Bigatti et al. | |
| 5,998,615 A | 12/1999 | Suarato et al. | |
| 6,087,340 A | 7/2000 | Gatti | |
| 6,096,888 A | 8/2000 | Suarato et al. | |
| 6,376,469 B1 | 4/2002 | Shimago et al. | |
| 6,653,455 B1 | 11/2003 | Johdo et al. | |
| 7,053,191 B2 | 5/2006 | Zabudkin et al. | |
| 2007/0037758 A1 | 2/2007 | Priebe et al. | |

FOREIGN PATENT DOCUMENTS

| | | |
|---|---|---|
| EP | 0328399 A2 | 8/1989 |
| WO | WO 86/00073 A1 | 1/1986 |
| WO | WO 96/29335 A1 | 9/1996 |

OTHER PUBLICATIONS

DuVernay et al., Cancer Research, 1980, 40: 387-394.*
Schmidt et al. , Preparative Carbohydrate Chemistry, 1997, p. 283-308.*
PCT International Search Report for PCT/US2004/20679, Applicant: Solux Corporation, Form PCT/ISA/220, dated May 4, 2006 (5 pages).
PCT Written Opinion for PCT/US2004/20679, Applicant: Solux Corporation, Form PCT/ISA/237, dated May 4, 2006 (4 pages).
Trimethylsilyl Trifluoromethanesulfonate as an Excelent Glucosidation Reagent for Antracycline Synthesis. Simple and Efficient Synthesis of Optically Pure 4-Demethoxydaunorubicin. Y. Kimura, M. Suzuki, T. Matsumoto, R. Abe, Sh. Terashima. Chem. Letters, 1984, pp. 501-504.
PCT International Search Report for PCT/US2006/07987, Applicant: Solux Corporation, Form PCT/ISA/220, dated Jul. 28, 2006 (4 pages).
PCT International Search Report for PCT/US2006/61978, Applicant: Solux Corporation, Forms PCT/ISA/210 and PCT/ISA/220, dated Jan. 10, 2008 (4 pages).
PCT Written Opinion for PCT/US2006/61978, Applicant: Solux Corporation, Form PCT/ISA/237, dated Jan. 10, 2008 (4 pages).
PCT Written Opinion for PCT/US2006/07987, Applicant: Solux Corporation, Form PCT/ISA/237, dated Jul. 28, 2006 (4 pages).
Office Action dated Jun. 13, 2006 for related U.S. Appl. No. 10/877,221, filed Jun. 25, 2004, Inventor: Victor Matvienko (7 pages).
Amendment dated Sep. 13, 2006 for related U.S. Appl. No. 10/877,221, filed Jun. 25, 2004, Inventor: Victor Matvienko (9 pages).
Office Action dated Oct. 24, 2006 for related U.S. Appl. No. 10/877,221, filed Jun. 25, 2004, Inventor: Victor Matvienko (7 pages).
Amendment dated Jan. 23, 2007 for related U.S. Appl. No. 10/877,221, filed Jun. 25, 2004, Inventor: Victor Matvienko (9 pages).
Office Action dated Mar. 16, 2007 for related U.S. Appl. No. 10/877,221, filed Jun. 25, 2004, Inventor: Victor Matvienko (6 pages).
Amendment dated Sep. 17, 2007 for related U.S. Appl. No. 10/877,221, filed Jun. 25, 2004, Inventor: Victor Matvienko (11 pages).
Declaration of Philipp Alexander Titulski under 37 C.F.R. § 1.132, dated Sep. 13, 2007, for related U.S. Appl. No. 10/877,221, filed Jun. 25, 2004, Inventor: Victor Matvienko (3 pages).
Declaration of Anil Dhedia under 37 C.F.R. § 1.132, dated Sep. 13, 2007, for related U.S. Appl. No. 10/877,221, filed Jun. 25, 2004, Inventor: Victor Matvienko (2 pages).
Declaration of Dr. Waldemar Priebe under 37 C.F.R. § 1.132, dated Sep. 15, 2007, for related U.S. Appl. No. 10/877,221, filed Jun. 25, 2004, Inventor: Victor Matvienko (38 pages).

(Continued)

*Primary Examiner* — Ileana Popa
(74) *Attorney, Agent, or Firm* — Vista IP Law Group LLP

(57) ABSTRACT

A method of preparing the anthracyclin carminomycin using a starting material comprising daunorubicin. The method comprises reacting daunorubicin or N-protected daunorubicin with soft Lewis acids for the demethylation of the 4-methoxy group, resulting in a reaction mass. The reaction mass is treated with an aqueous solution of a strong organic acid or a mineral acid. After decomposition of the resulting carminomycin and Lewis acids reactive complex, the reaction mass is extracted using a water insoluble organic solvent. As a result, carminomycin is extracted as a base.

8 Claims, No Drawings

(56) References Cited

OTHER PUBLICATIONS

Office Action dated Nov. 6, 2007 for related U.S. Appl. No. 10/877,221, filed Jun. 25, 2004, Inventor: Victor Matvienko (6 pages).

Office Action dated Dec. 11, 2007 for related U.S. Appl. No. 10/877,221, filed Jun. 25, 2004, Inventor: Victor Matvienko (4 pages).

Office Action dated Jun. 1, 2007 for related U.S. Appl. No. 11/367,742, filed Mar. 4, 2006, Inventor: Victor Matvienko (8 pages).

Amendment dated Dec. 3, 2007 for related U.S. Appl. No. 11/367,742, filed Mar. 4, 2006, Inventor: Victor Matvienko (10 pages).

Notice of Allowance dated Feb. 8, 2008 for related U.S. Appl. No. 11/367,742, filed Mar. 4, 2006, Inventor: Victor Matvienko (8 pages).

PCT International Search Report for PCT/US08/86088, Applicant: Solux Corporation, Form PCT/ISA/210 and 220, dated Jan. 26, 2009 (4 pages).

PCT Written Opinion of the International Search Authority for PCT/US08/86088, Applicant: Solux Corporation, Form PCT/ISA/237, dated Jan. 26, 2009 (3 pages).

PCT International Search Report for PCT/US2006/62286, Applicant: Solux Corporation et al., Forms PCT/ISA/220 and 210, dated Sep. 24, 2007 (3 pages).

PCT Written Opinion for PCT/US2006/62286, Applicant: Solux Corporation et al., Forms PCT/ISA/237, dated Sep. 24, 2007 (5 pages).

PCT International Preliminary Report on Patentability for PCT/US2006/62286, Applicant: Solux Corporation et al., Forms PCT/IB/326, 373 and PCT/ISA/237, dated Jul. 3, 2008 (7 pages).

PCT International Preliminary Report on Patentability for PCT/US2006/061978, Applicant: Solux Corporation et al., Forms PCT/IB/326, 373 and PCT/ISA/237, dated Jun. 26, 2008 (5 pages).

Amendment and Response dated Feb. 21, 2008 for U.S. Appl. No. 10/877,221, filed Jun. 25, 2004, inventor: Victor Matvienko (10 pages).

Office Action dated Jun. 9, 2008 for U.S. Appl. No. 10/877,221, filed Jun. 25, 2004, inventor: Victor Matvienko (5 pages).

Amendment After Final dated Aug. 1, 2008 for U.S. Appl. No. 10/877,221, filed Jun. 25, 2004, inventor: Victor Matvienko (7 pages).

Notice of Allowance dated Aug. 20, 2008 and Supplemental Notice of Allowability dated Oct. 31, 2008 for U.S. Appl. No. 10/877,221, filed Jun. 25, 2004, inventor: Victor Matvienko (10 pages).

\* cited by examiner

METHOD FOR PREPARING 4-DEMETHYLDAUNORUBICIN

RELATED APPLICATIONS

This Application claims the benefit of U.S. provisional Application No. 60/749,464, filed on Dec. 13, 2005, in accordance with 35 U.S.C. Section 119(e), and any other applicable laws. U.S. provisional Application No. 60/749,464 is hereby incorporated by reference in its entirety as if set forth fully herein.

FIELD OF THE INVENTION

The field of the invention generally relates to chemical methods used to produce anthracyclines, a compound which is useful as an anticancer chemotherapeutic drug. More specifically, the field of the invention relates to methods of producing cytostatic anthracyclin antibiotic 4-demethyldaunorubicin (commonly referred to as "carminomycin") in the form of Formula (1) (wherein An⁻ is an anion of any strong acid; for example, in one non-limiting case of 4'-epirubicin, An⁻ comprises Cl⁻).

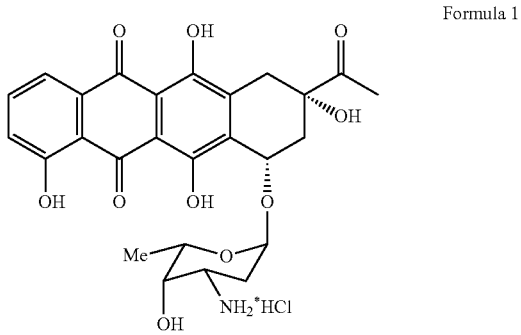

Formula 1

BACKGROUND OF THE INVENTION

Anthracyclines form one of the largest families of naturally occurring bioactive compounds. Several members of this family have shown to be clinically effective anti-neoplastic agents. These include, for example, daunorubicin, doxorubicin, idarubicin, epirubicin, pirarubicin, zorubicin, aclarubicin, and carminomycin. For instance, these compounds have shown to be useful in the treatment of breast carcinoma, acute lymphocytic and non-lymphocytic leukemia, chronic lymphocytic leukemia, non-Hodgkin's lymphoma, and other solid cancerous tumors.

Carminomycin (in the form of Formula (1)) is a well-known anthracyclin antibiotic that is used both in defined clinical applications and as a starting material for synthesis of multiple 4-modified anthracylins, and in particular, idarubicin (see for example, U.S. Pat. No. 7,053,191, the contents of which is hereby incorporated by reference herein in its entirety).

Microbiological production of carminomycin is complicated by a very low productivity of the known strains of microorganisms, at the level of 0.1-0.3 g/L. Up until the present, the synthetic method of preparing carminomycin has been very protracted (involving 10-12 chemical stages) and expensive. In the previously described methods of 4-methoxy group demethylation, the substrate was daunorubicinone because there had been no known methods of 4-methoxy group demethylation without breaking of the C-7 glycoside bond. The most common method of the 4-methoxy group demethylation involves treatment of the daunorubicinone with a strong Lewis acid, $AlCl_3$, in inert solvents such as chlorinated hydrocarbons (ex. dichloromethane) at boiling temperature. In an attempt to conduct the same synthesis with daunorubicin, the daunosamine glycoside bond is severed, and the anthracyclin nucleus is destroyed.

SUMMARY OF THE INVENTION

The present invention is directed to an innovative method for producing carminomycin using a novel method for the 4-methoxy group demethylation of a widely-available starting substance daunorubicin, that does not result in the destruction of the C-7 glycoside bond, and that decreases the number of synthesis stages from 10-12 to 1-3.

Demethylation is achieved by the treatment of daunorubicin or N-protected daunorubicin (Formula 2 and Formula 3, respectively) with soft Lewis acids, such as $TiHal_4$, $BHal_3$, $MgHal_2$, where Hal=F, Cl, Br, I in anhydrous solvents, such as alkanes, cycloalkanes, arenes, halogenoalkanes, simple ethers, $CS_2$, all of which are stable in Lewis acids, at temperatures 10-80° C.

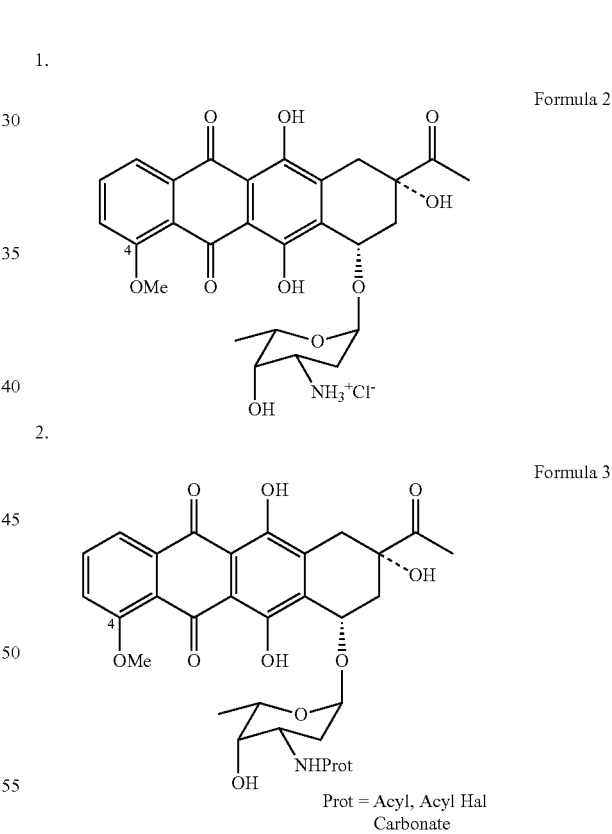

Extraction of carminomycin or N-protected carminomycin is achieved by treating the reaction mass with an aqueous solution of strong organic or mineral acids. After decomposition of the carminomycin and Lewis acids reactive complex, the reactive mass (in the case of utilization of water-soluble simple ethers) is extracted with water-insoluble (hydrophobic) organic solvents such as halogenoalkanes, cycloalkanes, arenes, $C_4$-$C_6$ alcohols and mixtures thereof. Carminomycin is then extracted as a base.

DETAILED DESCRIPTION OF THE INVENTION

The method of preparing a carminomycin compound using daunorubicin as the starting material according to the present invention comprises the following steps.

I. Demethylation of Daunorubicin or N-Protected Daunorubicin

The demethylation reaction is completed by treating daunorubicin or N-protected daunorubicin (Formula 2 and Formula 3, respectively) with soft Lewis acids, such as $TiHal_4$, $BHal_3$, $MgHal_2$, where Hal=F, Cl, Br, I in anhydrous solvents, such as alkanes, cycloalkanes, arenes, halogenoalkanes, simple ethers, $CS_2$, all of which are stable in Lewis acids, at temperatures in the range of about 10-80° C. (as shown in Diagram 1).

Diagram 1

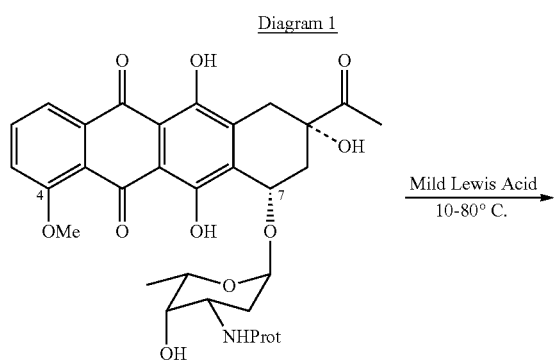

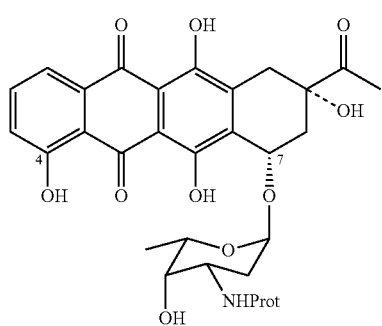

Prot = H, Acyl, Acyl Halide, Carbonate

With utilization of the N-protected daunorubicin, the reaction is accomplished with lesser amounts of by-products (impurities) and a higher yield.

The amount of Lewis acid used in the reaction is 1-5 moles per 1 mole of daunorubicin, preferably 1.5-3 moles.

The reaction temperature depends on the strength of the Lewis acid and must provide for the maximum regioselectivity of the process involving breakage of the 4-OMe bond with preservation of the 7-O-daunosamine bond, preferably 40-60° C.

The solvents suitable for conduction of the reaction are selected based on the same principles as for the temperature selection. Preference is given to halogenoalkanes, simple ethers, and $CS_2$.

Extraction of carminomycin or N-protected carminomycin is performed by treating the reaction mass with an aqueous solution of strong organic acids, such as oxalic acid, trifluoroacetic acid or such mineral acids as sulfuric acid or hydrochloric acids pH 2.5±1. After decomposition of the carminomycin and Lewis acids reactive complex, the reactive mass (in the case of utilization of water-soluble simple ethers) is extracted with water-insoluble (hydrophobic) organic solvents such as halogenoalkanes, cycloalkanes, arenes, $C_4$-$C_6$ alcohols and mixtures thereof. Carminomycin may then be extracted as a base.

The 3'N-Prot-group, in the case of utilization of N-protected daunorubicin, is removed immediately upon completion of the synthesis or after further modification of the 4-R substituent, depending on the goals of synthesis.

Example 6.25 grams of N-trifluoroacetyldaunorubicin is dissolved in 150 ml of tetrahydrofurane, and 2.9 grams of unhydrous magnesium chloride is slowly added under conditions that exclude contact with atmospheric moisture. The resulting mixture is incubated for 1.5 hours at 40° C., then poured into ice water, titrated to pH 2.5 with trifluoroacetic acid, and then extracted with 2×50 ml aliquots of dichloromethane. The organic layer is separated and dried with anhydrous $MgSO_4$. The solvent is then evaporated at below-atmospheric pressure. The result is about 4.8 grams of N-TFA-carminomycin with purity of about 65-80% (this is confirmed by HPLC).

The N-TFA-carminomycin, obtained from the above synthesis, is then suspended in 200 ml of distilled water at a temperature of 30° C., and 15 ml of 1.0 N NaOH solution is added. The mixture is incubated for 30 minutes and then neutralized to pH 7 with a solution of hydrochloric acid and is then sent to preparative chromatography. After evaporation of eluate, 3.0-3.8 grams of carminomycin is produced with a purity of about 96% (this is confirmed by HPLC).

We claim:

1. A method of preparing the anthracyclin Carminomycin represented by Formula 1 as shown below,

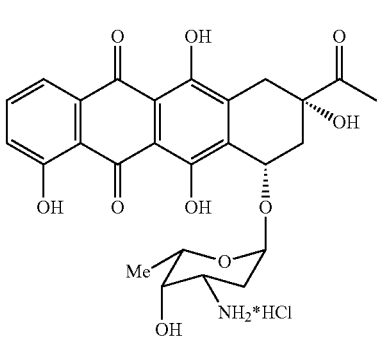

Formula 1 from anthracyclin daunorubicin, comprising the following step:
reacting one of daunorubicin represented by Formula 2,

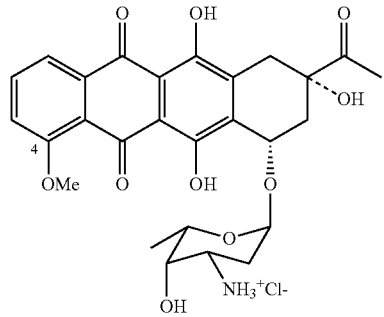

or N-protected daunorubicin represented by Formula 3,

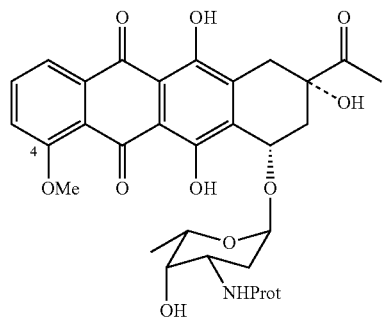

Prot = Acyl, Acyl Halide, Carbonate with a soft Lewis acid for the demethylation of the 4-methoxy group of said one of daunorubicin represented by Formula 2, or N-protected daunorubicin represented by Formula 3, resulting in a reaction mass.

2. The method of claim 1, wherein the soft Lewis acid is selected from the group of: $TiHal_4$, $BHal_3$, $MgHal_2$ where Hal=F, Cl, Br, I.

3. The method of claim 1, wherein the reaction is conducted using a solvent selected from the group of: anhydrous alkanes, cycloalkanes, arenes, halogenoalkanes, simple ethers, or $CS_2$.

4. The method of claim 1, wherein the reaction is conducted at a temperature of about 10 to about 80° C. for between 1 to 10 hours.

5. The method of claim 1, further comprising the steps of:
treating the reaction mass with an aqueous solution of one of strong organic acid or mineral acid; and
extracting carminomycin as a base from the treated reaction mass using a water-insoluble organic solvent.

6. The method of claim 5, wherein said one of strong organic acid or mineral acid is selected from the group consisting of sulfuric acid or hydrochloric acid.

7. The method of claim 5, wherein said water-insoluble organic solvent comprises one of halogenoalkanes, cycloalkanes, arenes, $C_4$-$C_6$ alcohols, or mixtures of the preceding.

8. A method of preparing the anthracyclin Carminomycin represented by Formula 1 as shown below,

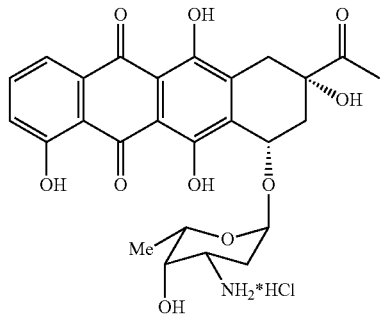

from anthracyclin daunorubicin, comprising the following steps:
reacting one of daunorubicin represented by Formula 2,

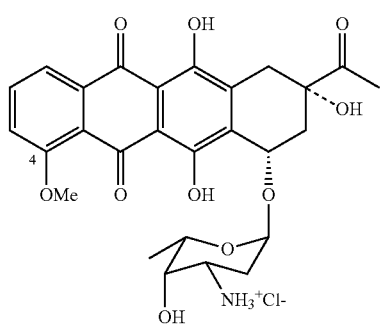

or N-protected daunorubicin represented by Formula 3,

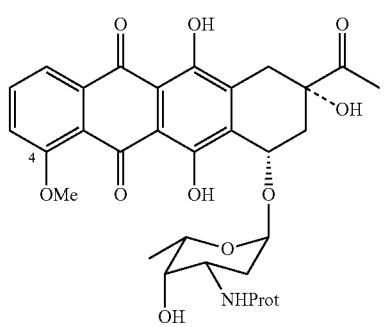

Prot = Acyl, Acyl Halide, Carbonate with a soft Lewis acid, the soft Lewis acid is selected from the group of $TiHal_4$, $BHal_3$, $MgHal_2$ where Hal=F, Cl, Br, I, for the demethylation of the 4-methoxy group of said one of daunorubicin represented by Formula 2, or N-protected daunorubicin represented by Formula 3, the reaction being conducted using a solvent selected from the group of anhydrous alkanes, cycloalkanes, arenes, halogenoalkanes, simple ethers, or $CS_2$, and the reaction conducted at a temperature of about 10 to about 80° C. for between 1 to 10 hours, thereby resulting in a reaction mass;
treating the reaction mass with an aqueous solution of an acid selected from the group consisting of sulfuric acid or hydrochloric acid; and extracting carminomycin as a base from the treated reaction mass using a water-insoluble organic solvent selected from the group of halogenoalkanes, cycloalkanes, arenes, $C_4$-$C_6$ alcohols, or mixtures of the preceding.

* * * * *